United States Patent [19]

Moroney et al.

[11] Patent Number: 4,603,486

[45] Date of Patent: Aug. 5, 1986

[54] AUTOMATED ANTHROPOMETRIC DATA MEASUREMENT SYSTEM

[75] Inventors: William F. Moroney, Chalfont, Pa.; James C. Bartholomew, Burke; Clifford M. Cagle, Reston, both of Va.; Robert E. Hughes, Albuquerque, N. Mex.

[73] Assignee: The United States of America as represented by the Secretary of the Navy, Washington, D.C.

[21] Appl. No.: 788,371

[22] Filed: Oct. 17, 1985

[51] Int. Cl.⁴ ............................................... A61B 5/10
[52] U.S. Cl. ..................................... 33/512; 128/774; 128/781
[58] Field of Search ............. 33/512, 511, 515, 169 R, 33/143 C; 128/774, 779, 781, 782

[56] References Cited

U.S. PATENT DOCUMENTS

| | | | |
|---|---|---|---|
| 3,196,551 | 7/1965 | Provost et al. | 128/774 |
| 3,575,159 | 4/1971 | Pile | 128/774 |
| 3,667,561 | 6/1972 | Hutchinson et al. | 33/512 |
| 3,693,265 | 9/1972 | Alexander | 33/512 |
| 3,722,103 | 3/1973 | Gregoire | 33/512 |
| 4,033,329 | 7/1977 | Gregory | 128/781 |
| 4,033,336 | 7/1977 | Murawski et al. | 33/512 |
| 4,134,213 | 1/1979 | Kushmuk | 33/169 R |
| 4,425,713 | 1/1984 | Rotella | 33/512 |
| 4,492,236 | 1/1985 | Pice | 128/781 |

Primary Examiner—Willis Little
Attorney, Agent, or Firm—Robert F. Beers; Henry Hansen; James R. Burdett

[57] ABSTRACT

An automated anthropometric data measurement system includes a standing measuring assembly and a seated measuring assembly to determine pertinent anthropometric features of aviators being screened for assignment to particularly suitable aircraft. Both assemblies have a plurality of position sensors and measuring probes which are selectively placed by an operator upon the aviator, each measuring probe producing a digital data signal indicative of the particular feature measured when selective position sensors indicate body contact. The signals are then collected by a microcomputer which compares them to a predetermined population and outputs the compared data to magnetic storage media.

6 Claims, 3 Drawing Figures

AUTOMATED ANTHROPOMETRIC DATA MEASUREMENT SYSTEM

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention is related generally to devices used in the measurement and delineation of naturally developed characteristics and formations of the human body, and more specifically to a system for reliably and accurately measuring selected anthropometric features in order to screen personnel for assignment to particularly suitable workspaces.

Anthropometry, or the body of knowledge pertaining to human body measurements, plays an important role in the design of many products. Different products, however, require differing levels of accommodation to the sizes and proportions of the human body. For instance, if the product is rather simple, the effort that is generally devoted to such accommodation is usually relatively inexpensive and successful. On the other hand, if the product is a highly complex system such as an aircraft, the attainment of a high level of accommodation almost invariably requires expensive economic and engineering trade-offs with varying levels of success. For a more detailed treatment of the inherent difficulties in aircraft design, see Kennedy, Kenneth W. "International Anthropometric Variability and Its Effect on Aircraft Cockpit Design" In: Chapanis, Alphone, *Ethnic Variables in Human Factors Engineering* (Baltimore, Johns Hopkins University Press, 1975) TA 166.E83.

Fortunately in a great many cases the human body can make some accommodation to an inadequately designed system. There are, nevertheless, some instances in which very nearly all those not readily accommodated will not be able to operate an aircraft or workstation safely and efficiently. Examples are inadequate reach distance to critical hand and foot controls, inadequate ejection clearance, and excessive seat-to-canopy distance. Anthropometric dimensions have in the past been obtained through the use of anthropometers and calipers to measure the lineal and circumferential dimensions of those persons intending to fly the particular aircraft under design. Those devices, however, required skilled operators and a time-consuming process in which a number of predetermined anthropometric features were measured. A false reading could be obtained by the failure of the operator to properly position the device upon that part of the body being measured, or by failing to ascertain that the subject was properly positioned.

SUMMARY OF THE INVENTION

Accordingly, it is a general purpose and object of the present invention to provide an apparatus for reliably and accurately measuring selected anthropometric features in order to screen personnel for assignment to particularly suitable workspaces. More specifically, the object of this invention is to provide a means of rapidly screening aviators for assignment to individual aircraft types. Additionally, data describing the aviator population can be gathered for future use.

Briefly, these and other objects of the present invention are accomplished by a microprocessor-controlled, automated anthropometric data measurement system including two major functional subsystems: a standing measuring assembly and a seated measuring assembly. Each assembly further includes a plurality of position sensors for ensuring the proper positioning of the tested subject, and a plurality of measuring probes having an encoding device for determining the measurement of interest.

An operator inserts the subject's identification into an ID entry device, where upon the subject may assume the required position as instructed by the operator. The position sensors, in conjunction with a subject's positioning aid which is observable by the subject, provide a go-no go means of ensuring that the subject is properly positioned. When the respective sensors indicate such, the operator moves a measuring probe into position, thus, determining the anthropometric feature of interest and feeding it via an encoding device to a microcomputer acting as the system controller. The system controller then operates upon the input data, running various reasonability checks to ensure the data falls within predetermined ranges, and outputs it to a preselected storage media such as a magnetic disk or standardized form.

Other objects, advantages and novel features of the invention will become apparent from the following detailed description of the preferred embodiment when considered in conjunction with the accompanying drawings wherein:

DETAILED DESCRIPTION OF THE PREFERRED EMBODIMENT

Figure 1:
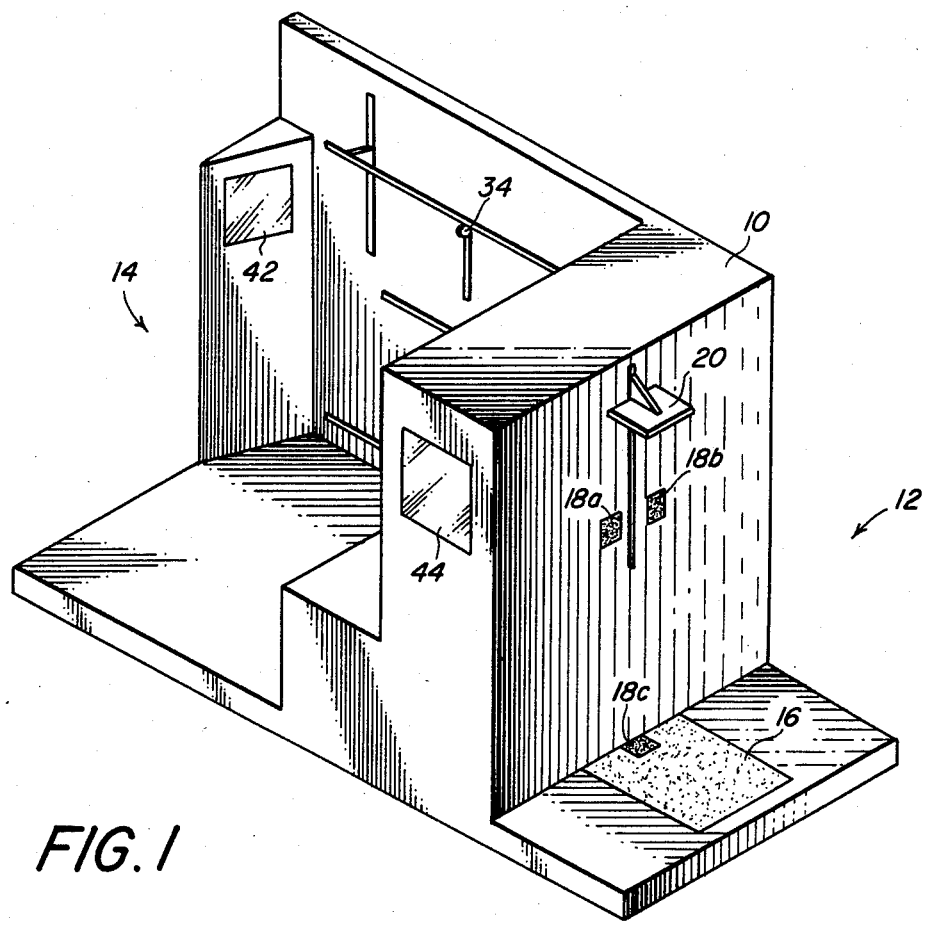
FIG. 1 is one perspective of a preferred embodiment of an automated anthropometric data measurement system (AADMS) according to the present invention.
Figure 2:
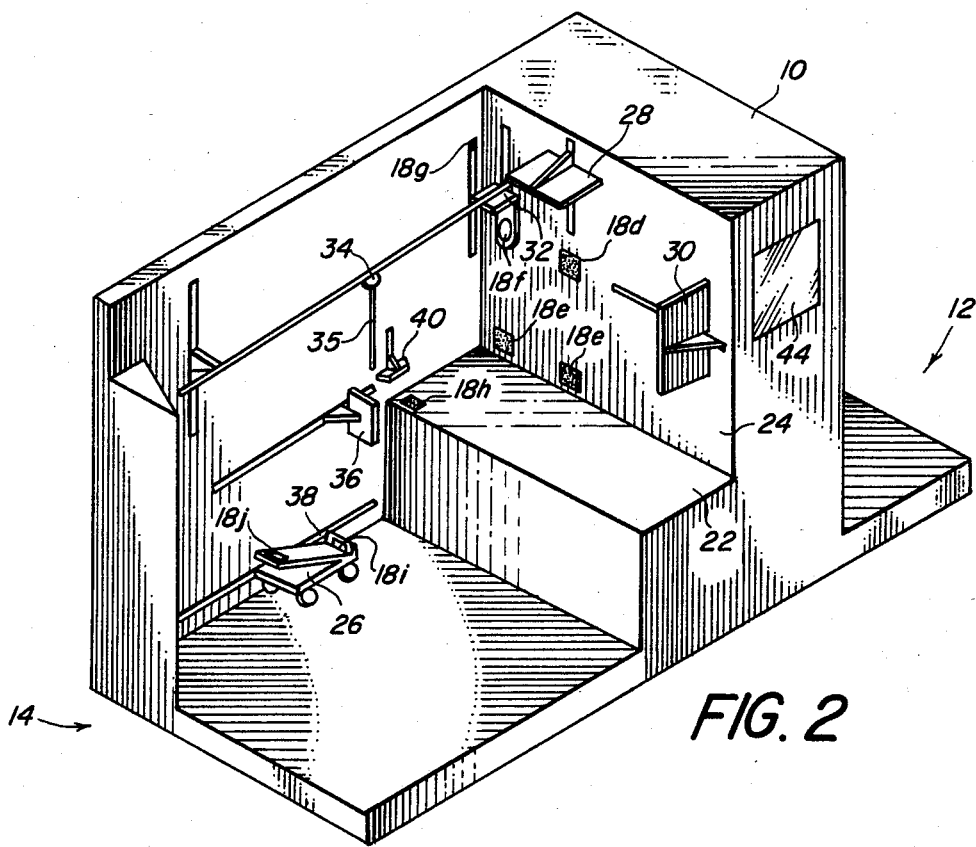
FIG. 2 is another perspective of the AADMS shown in FIG. 1.

Referring now to the drawings, wherein like characters designate like or corresponding parts throughout the several views, there are shown in FIGS. 1 and 2 two perspectives of an automated anthropometric data measurement system (AADMS) 10 according to the present invention and including, in general, a standing measuring assembly 12 and a seated measuring assembly 14. As is shown in FIG. 1, the standing measuring assembly 12 has a conventional load cell 16 or similar such device for determining the weight of a subject (not shown), and three position sensors 18a, 18b, and 18c which are used in conjunction with a counterbalanced or spring-loaded ST measuring probe 20 to determine the subject's stature (ST) as defined in Table I.

TABLE I

| Dimension | Definition |
| --- | --- |
| Stature (ST) | The vertical distance from the floor to a measuring probe placed firmly against the subject's scalp, while the subject stands erect with his back, shoulders, and heels firmly positioned against the vertical plane. |
| Functional Arm Reach (FAR) | The distance from the vertical plane to the point where the thumb and index finger are |

TABLE I-continued

| Dimension | Definition |
| --- | --- |
| | pressed together such that the greatest horizontal distance from the vertical plane is obtained while the subject is sitting erect, looking directly forward, with his head, shoulders, back, and buttocks firmly positioned against the seat back. The subject's feet should be resting flat on the floor. |
| Sitting Height (SH) | The distance between the seat surface and the top of the head when the subject is sitting erect, looking directly forward, with his head, shloulders, back, and buttocks, firmly positioned against the seat back. The subject's feet should be resting flat on the floor. |
| Shoulder Height Sitting (SHS) | The distance from the seat surface to the top of the acromial process on the right shoulder when the subject is sitting erect with his back, shoulders, and buttocks firmly positioned against the seat back. The subject's feet should be resting flat on the floor. |
| Shoulder Width (SW) | The distance across the shoulders between the greatest protrusion of the deltoid muscles. It is measured with the subject sitting so that his shoulders, back, and buttocks are firmly positioned against the seat back; upper arms hanging at his sides and forearms extended forward. Subject's lungs should be fully expanded. |
| Buttock Knee Length (BKL) | The distance from the back of the right buttock to the front of the right kneecap with the subject sitting erect with his back, shoulders, and buttocks firmly positioned against the seat back. The subject's feet should be resting flat on the floor of the platform. |
| Functional Leg Reach (FLR) | The distance from the right buttock to the pivot point on a brake/rudder pedal assembly when the leg is extended as far as possible, while the subject is sitting erect with his back, shoulders, and buttocks firmly positioned against the seat back and his thigh positioned against the seat pan. |
| Knee Height, Sitting (KHS) | The distance from the footrest surface to the musculature just above the knee. It is measured with the subject sitting such that his shoulders, back, and the buttocks are firmly positioned against the seat back and his knee is bent to form a 90° angle. |

The subject, following an operator's instructions, assumes an erect position upon the load cell 16 with his back flush to the upright position of the standing measuring assembly 12, touching sensors 18a and 18b and placing his heels together on the sensor 18c. While a simple microswitch may be used for the standing heel sensor 18c, the standing back sensors 18a and 18b are perfectly formed of a matrix of such switches. Once the subject is properly positioned, as determined by the simultaneous closure of the sensors 18a, 18b, and 18c, and as indicated to the operator on his Operator's Display and Control Panel 44, the operator lowers the ST probe 20 until it touches the top of the subject's head. In order to assist the operator in ensuring that the subject is properly positioned, the Operator's Display and Control Panel 44 includes a conceptual view of the subject with a number of red/green (go/no go) indicator lights equal to the number of position sensors. For example, by examining the view present when measurements such as the functional arm reach and functional leg reach are taken, the operator can detect unacceptable rotation of the hip or shoulder which would lead to an erroneously high value for these anthropometric dimensions. An optical or potentiometric encoding device (not shown) is attached to the ST probe 20 such that movement of the ST probe 20 causes a concomitant change in the value sensed by the encoding device. For example, assuming that the encoding device is preset to a value of 84 inches, a ten-inch downward movement of the ST probe 20 to the top of the subject's head would indicate that the subject is 74 inches tall.

As shown more clearly in FIG. 2, the seated measuring assembly 14 is formed with a seat pan portion 22 and a seat back portion 24, and generally includes an adjustable foot pedal 26, and a plurality of position sensors 18d through 18j which are used in conjunction with a plurality of measuring probes 28, 30, 32, 34, 36, 38, and 40 to determine the remaining anthropometric features delineated in Table I as is discussed in further detail hereinbelow. Position sensors 18d through 18j may be configured similarly to the standing back sensors 18a and 18b, or may include a matrix which allows a small current to flow through the subject's back, ensuring continuity when his back is positioned properly, while the probes 28, 30, 32, 34, 36, 38, and 40 include encoding devices as used in the ST probe 20.

In order to determine the subject's sitting height (SH), the operator will instruct the subject to sit upon the seat pan portion 22 with his back and buttocks positioned to close the left shoulder blade sensor 18d, two buttock sensors 18e, and the right shoulder blades sensor 18f. A conceptual view of the seated subject with a number of indicator lights equal to the number of position sensors 18d through 18j is displayed on a Subject's Positioning Aid 42 which is situated to permit continuous observation by the subject during his evaluation. For example, a red/green indicator may be used for each position sensor 18d through 18j to indicate whether it is open or closed. When all four sensors 18d, 18e, and 18f are simultaneously closed, the operator lowers the SH measuring probe 28 to the top of the subject's head thus measuring his sitting height (SH) in a manner analogous to that described for the stature (ST) measurement.

The subject's shoulder width (SW), shoulder height sitting (SHS), and buttock-knee length (BKL) are similarly determined. For shoulder width (SW), the left shoulder blade sensor 18d, buttock sensors 18e, right shoulder blade sensor 18f, and the right shoulder wall sensor 18g must be closed before the operator can positon the SW measuring probe 30 against the subject's left shoulder. The same sensors 18d, 18e, 18f, and 18g must be closed prior to the operator's lowering of the SHS measuring probe 32 to the top of the subject's right shoulder in order to determine his shoulder height sitting (SHS). Likewise, in order to determine the subject's buttock-knee length (BKL), the seat back sensor 18d, buttock sensors 18e, and the thigh sensor 18h must be closed before the operator positions the BKL measuring probe 36 against the subject's right knee.

For a determination of the subject's functional arm reach (FAR), the left shoulder blade sensor 18d, buttock sensors 18e, and right shoulder blade sensor 18f must first be closed. The operator then instructs the subject to extend his right arm fully, keeping sensors 18d, 18e, and 18f closed, such that the juncture of his thumb and index finger touches a vertical extension 35 of the FAR Measuring probe 34. In order to determine the subject's functional leg reach (FLR), the left shoulder blades sensor 18d, buttock sensors 18e, thigh sensor 18f, and the heel and toe sensors 18i and 18j located on the pedal assembly 26 must be closed while the subject extends his right leg as far as he can while keeping his foot on the pedal assembly 26 which includes the FLR measuring probe 38. Likewise, the left shoulder blade sensor 18d, buttock sensors 18e, and thigh sensor 18f must be closed while the operator positions the KHS measuring probe 40 to the top of the subject's right knee in order to determine the subject's knee height sitting. A summary of the position sensor setting required for each anthropometric characteristic is presented in Table II.

within the system controller 50 prevent values such as sitting heights greater than 44 inches or less than 30 inches from being entered into the AADMS 10. These minimum-maximum values are based on data associated with similar male and female populations. On the other hand, in order to verify that sufficient differences exist between various anthropometric measurements, an-

TABLE II

| Position Sensors | Position Sensor Number | ANTHROPOMETRIC FEATURE | | | | | | | |
|---|---|---|---|---|---|---|---|---|---|
| | | Stature | Sitting Height | Shoulder Width | Shoulder Height Sitting | Functional Arm Reach | Buttock-Knee Length | Functional Leg Reach | Knee Height Sitting |
| Standing Heel | 18c | X | | | | | | | |
| Standing Back | 18a, 18b | X | | | | | | | |
| Left Shoulder Blade | 18d | | X | X | X | X | X | X | X |
| Buttocks | 18e | | X | X | X | X | X | X | X |
| Right Shoulder Blade | 18f | | X | X | X | X | | | |
| Right Shoulder (Wall) | 18g | | | X | X | | | | |
| Thigh | 18h | | | | | | X | X | X |
| Heel (Pedal) | 18i | | | | | | | X | |
| Toe | 18j | | | | | | | X | |

Figure 3:
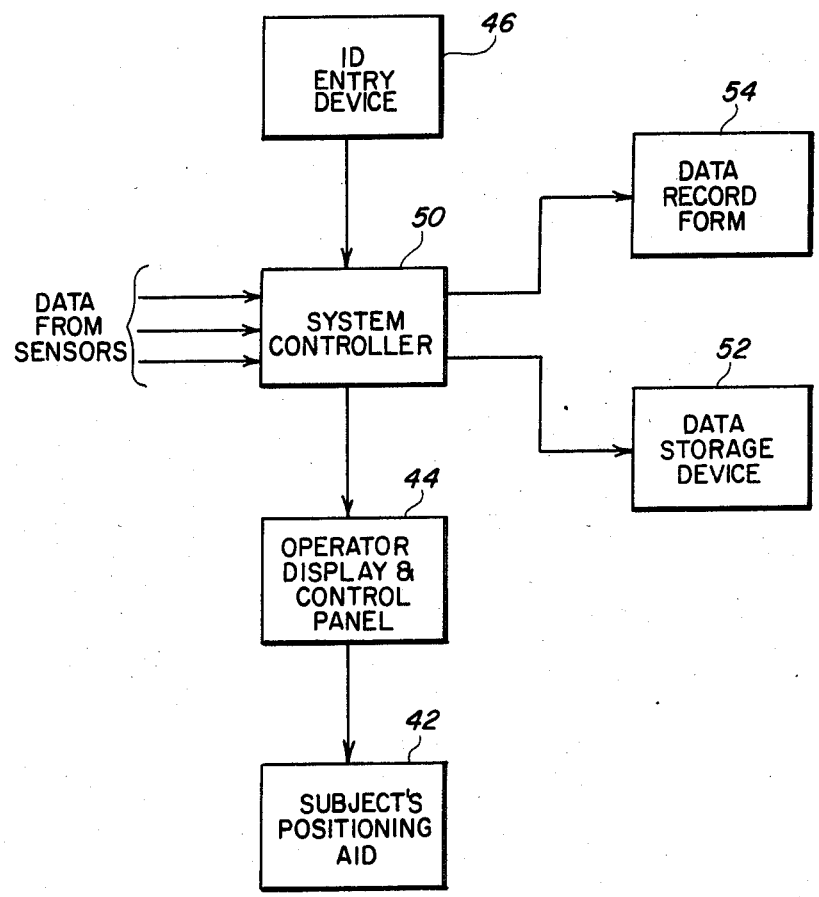
FIG. 3 is a block diagram of the AADMS shown in FIGS. 1 and 2.

Having explained in some detail the structural features of the present invention, its operation will now be summarized with reference to FIG. 3. The operator first enters the subject's identification into the AADMS 10 at an ID entry device 46, either manually or through the insertion of a pass card into a conventional card reader. An indication of the subject's identification is subsequently displayed via a conventional microcomputer or system controller 50 on an ID and Measurement Readout 48 located on the Operator's Display and Control Panel 44.

The subject then assumes the required position, following operator instructions, in either the standing measuring assembly 12 or the seated measuring assembly 14 and ensures that the applicable position sensors are closed by observing the Subject's Positioning Aid 42. When the subject is positioned correctly and the appropriate measuring probe is in place, data are allowed to flow to the system controller 50 from the respective encoding device attached to each probe. If the required position sensors have not been closed, the necessary corrective action (i.e., a red light indicating which sensors needs to be closed) is displayed on the Operator's Display and Control Panel 44. Anthropometric data will be recorded only when the subject is positioned correctly.

After the system controller 50 receives the data from the particular measuring probe and displays that data on the Operator's Display and Control Panel 44, the controller 50 executes a number of data reasonability checks, such as determining whether the data are in range of known anthropometric valves and whether certain related measurements such as sitting height and shoulder height sitting have sufficient differences between them. If a discrepancy is noted, it will also be displayed on the Operator's Display and Control Panel 44.

For example, in order to verify that the data are within acceptable ranges, a series of checking routines other series of routines within the system controller 50 will, for example, ensure that the sitting height minus the shoulder height sitting must be at least 9.9 inches and connot exceed 14.3 inches. These routines are, again, based on similar data from the general population.

When data from each of the anthropometric features listed in Table I have successfully been collected, such observed data is compared in the system controller 50 to a prediction model stored therein. If the differences between the observed and the predicted values do not exceed a set of predetermined limits, then the data are accepted and stored on a data storage device 52 such as a magnetic disk or recorded on a standardized anthropometric data record form 54. For example, by inserting the required values into prestored, conventional regression equations, predicted anthropometric dimensions can be obtained. If the predicted stature were assumed to be equal to the sitting height plus the functional leg reach plus a predetermined constant, and the measured value fell within a predetermined range around the predicted value, then the system controller 50 would consider it valid. While the AADMS 10 is designed to work normally in an automatic mode, a manual mode is provided as a back-up in the preferred embodiment of the present invention. In the manual mode the data are copied manually onto an appropriate record form.

Some of the many advantages of the invention should now be readily apparent. For example, a novel system has been provided which is capable of quickly and reliably determining selected anthropometric features for use in screening aviators for assignment to the respective aircraft. Moreover, the system provided is adaptable to magnetic storage media.

Obviously many modifications and variations of the present invention are possible in light of the above teachings. It is therefore to be understood that within the scope of the appended claims, the invention may be practiced otherwise than as specifically described.

What is claimed is:

1. An anthropometric data measurement system for screening an aviator for subsequent assignment to a particularly suitable aircraft, comprising in combination:
   a first measuring assembly for determining the aviator's stature;
   a second measuring assembly including a seat, having a seat pan portion and a seat back portion, and a pedal assembly for determining the aviator's sitting height, shoulder height sitting, shoulder width, functional arm reach, buttock-knee length, functional leg reach, and knee height sitting;
   a display and control panel for assisting an operator in the correct placement of the aviator and selecting the respective anthropometric feature to be measured;
   a positioning aid observable by the aviator for assisting him in maintaining a position required for the respective anthropometric feature to be measured;
   system controller means for collecting the measurements determined by said first and second measuring assemblies, comparing the collected measurements to a predetermined set of upper and lower limits, performing data reasonability checks and outputting said collected measurements when they fall within said predetermined set of upper and lower limits; and
   archival means for storing the measurements output from said system controller means.

2. A system according to claim 1, wherein said first measuring assembly comprises:
   a first base member;
   a back member mounted on and extending vertically upward from said base member;
   a stature measuring probe slidably mounted within and disposable vertically along an axis bisecting said back member for producing a digital data signal indicative of the aviator's stature;
   a pair of standing shoulder position sensors, each including a matrix of microswitches mounted on said back member;
   a standing heel position sensor including a microswitch mounted on said base member at the point at which it intersects the back member;
   wherein said digital data signal indicative of the aviator's stature is output from said stature measuring probe to said system controller means when said pair of shoulder position sensors and said standing heel position sensor are simultaneously closed.

3. A system according to claim 2, wherein said first measuring assembly further comprises a load cell mounted within said base member to determine the aviator's weight and produce a digital data signal indicative thereof.

4. A system according to claim 1, wherein said second measuring assembly comprises:
   a second base member upon which said seat is mounted;
   a side member mounted on and extending vertically upward from said second base member, said side member abutting the right side of said seat;
   a sitting height measuring probe slidably mounted within and disposable vertically along said seat back portion for producing a digital data signal indicative of the aviator's sitting height;
   a shoulder width measuring probe slidably mounted within and disposable horizontally along said seat back portion for producing a digital data signal indicative of the aviator's shoulder width;
   a shoulder height sitting measuring probe slidably mounted within and disposable vertically along said seat back portion for producing a digital data signal indicative of the aviator's shoulder height sitting;
   a functional arm reach measuring probe slidably mounted and disposable horizontal along said side member for producing a digital data signal indicative of the aviator's functional arm reach;
   a buttock knee length measuring probe slidably mounted within and disposable horizontally along said side member for producing a digital data signal indicative of the aviator's buttock knee length;
   a functional leg reach measuring probe attached to said pedal assembly for producing a digital data signal indicative of the aviator's functional leg reach;
   a knee height sitting measuring probe slidably mounted within and disposable vertically along said side member for producing a digital data signal indicative of the aviator's knee height sitting;
   a pair of buttocks position sensors, each including a matrix of microswitches mounted on said seat back portion;
   a left shoulder blade position sensor including a matrix of microswitches mounted on said seat back portion at a point approximately where the seated aviator's left shoulder blade would touch;
   a right shoulder blade position sensor including a matrix of microswitches mounted on said shoulder height sitting measuring probe;
   wherein said digital data signals indicative of the aviator's sitting height and functional arm reach are output from their respective measuring probe to said system controller means when said pair of buttocks position sensors, and said left and right shoulder blade position sensors are simultaneously closed;
   a right shoulder wall position sensor including a matrix of microswitches mounted on said side member at a point approximately where the seated aviator's right shoulder would touch;
   wherein said digital data signals indicative of the aviator's shoulder width and shoulder height sitting are output from their respective measuring probe to said system controller means when said pair of buttocks position sensors, said left and right shoulder blade position sensors, and said right shoulder wall position sensor are simultaneously closed;
   a thigh position sensor including a matrix of microswitches mounted on said seat pan portion at a point approximately where the seated aviator's right thigh would touch;
   wherein said digital data signals indicative of the aviator's buttock knee length and knee height sitting are output from their respective measuring probe to said system controller means when said pair of buttocks position sensors, said left shoulder blade position sensor, and said thigh positon sensor are simultaneously closed;
   a pair of pedal position sensors, one mounted at the heel and one at the toe of said pedal assembly;

wherein said digital data signal indicative of the aviator's functional leg reach is output from said functional leg reach measuring probe to said system controller means when said pair of buttocks position sensors, said left shoulder blade position sensor, said thigh position sensor, and said pair of pedal positon sensors are simultaneously closed.

5. A system according to claim 1, wherein said system controller means further comprises:
a display and control panel situate between said first and second measuring asemblies for selecting the anthropometric feature to be measured, indicating the state of each position sensor, and displaying the numeric value of the collected measurement.

6. A system according to claim 1, wherein said archival means comprises a magnetic storage medium.

* * * * *